US00PP27978P3

(12) United States Plant Patent
Defranceschi

(10) Patent No.: US PP27,978 P3
(45) Date of Patent: May 9, 2017

(54) APPLE TREE NAMED 'GALA 2013'

(50) Latin Name: *Malus domestica Borkh*
Varietal Denomination: Gala 2013

(71) Applicant: GRIBA Baumschule Landwirtschaftliche Gesellschaft, Terlan (IT)

(72) Inventor: Alois Defranceschi, Leifers (IT)

(73) Assignee: GRIBA Baumschule Landwirtschaftliche Gesellschaft, Terlan, BZ (IT)

( * ) Notice: Subject to any disclaimer, the term of this patent is extended or adjusted under 35 U.S.C. 154(b) by 97 days.

(21) Appl. No.: 14/544,985

(22) Filed: Mar. 12, 2015

(65) Prior Publication Data

US 2016/0088783 P1 Mar. 24, 2016

(30) Foreign Application Priority Data

Sep. 19, 2014 (IT) ..... BZ2014V0002

(51) Int. Cl.
*A01H 5/08* (2006.01)

(52) U.S. Cl.
USPC ..... Plt./162

(58) Field of Classification Search
USPC ..... Plt./162
See application file for complete search history.

*Primary Examiner* — Keith Robinson
(74) *Attorney, Agent, or Firm* — Myers Bigel, P.A.

(57) ABSTRACT

*Malus domestica* Borkh 'Gala 2013' variety is distinguished from the original mother plant 'Gala Standard' and other Gala varieties by an intense solid flush purple-red over-colour that covers 100% of the surface of all the fruits on the trees at harvesting time, an intense solid flush red colour of the fruits already 30 days before harvesting time, at full blooming the receptacle assumes a red coloration, the young fruits 40 days after full blooming are already red coloured, and the petiole and central vein are red coloured on the lower side of the fully expanded leaves.

10 Drawing Sheets

Latin name of the genus and species: The Latin name of the genus and species of the plant variety disclosed herein is *Malta domestica* Borkh.

Variety denomination: The inventive cultivar of *Malus domestica* Borkh disclosed herein has been given the varietal denomination 'Gala 2013'.

RELATED APPLICATION INFORMATION

This application claims priority under 35 U.S. §119(a) to Italian Plant Breeders' Rights Application No. BZ2014V000002, filed Sep. 19, 2014; the disclosure of which is incorporated herein by reference in its entirety.

BACKGROUND OF THE INVENTION

The present invention relates to a new and distinct Gala variety of apple tree named 'Gala 2013'. The new variety was discovered as a sport limb mutation on a 'Gala Standard' variety plant (not patented), in a field in Laives area, Bolzano province, Italy. The mutated branch was identified 30 days before the harvesting time and noticed because of the anticipated solid flush red (RHS 53B) coloration of the fruits when compared to the other fruits on the plant still green (RHS 145B) (FIG. 1). At harvesting time, the fruits on the mutated branch appeared dark purple-red coloured (RHS 60A) on 100% of the surface without stripes.

The mutation was first asexually propagated in August 2009 and 15 trees were initially grown in a Griba property field located in Gazzo Veronese in Verona province, Italy. The first observed fruiting of the propagated trees occurred in the 2011 season and confirmed the dark purple-red coloured (RHS 60A) at harvesting time on 100% of the fruit without stripes and the stability of the mutation In the next years, additional 'Gala 2013' trees have been asexually propagated, planted and evaluated in different Griba property fields in Bolzano province and Verona province, Italy. All of the trees of 'Gala 2013' have been observed to remain true to type over successive asexually propagated generations and maintain the intensity of their characteristic dark purple red colour (RHS 60A) on 100% of the fruit without stripes.

SUMMARY OF THE INVENTION

The new variety 'Gala 2013' is distinguished from the original mother plant 'Gala Standard' and other Gala varieties by the following unique combination of characteristics:

- intense solid flush purple-red over-colour (RHS 60A) that covers 100% of the surface of all the fruits on the trees at harvesting time (FIGS. 2, 6 and 7);
- intense solid flush red colour (RHS 53B) of the fruits already 30 days before harvesting time (FIG. 10);
- at full blooming the receptacle assumes a red coloration (RHS 60C) (FIG. 4);
- the young fruits 40 days after full blooming are already red coloured (RHS 46A) (FIG. 5); and
- the petiole and central vein are red coloured (RHS 61B) on the lower side of the fully expanded leaves (FIG. 2).

The new variety 'Gala 2013' can be distinguished from 'Galaval' (U.S. Plant Pat. No. 19,909) by the dark purple-red over-colour (RHS 60A) of 'Gala 2013' fruits compared to dark purple-brown colour (RHS 59A) of 'Galaval' fruits. 'Gala 2013' fruits assume a solid flush red (RHS 53B)

coloration 30 days before ripening, much earlier than 'Gala-val'. On 'Gala 2013', the fruit red colour (RHS 60A) is always solid flush without observation of stripes also during the colour accumulation one month before harvesting.

The new variety 'Gala 2013' can be distinguished from all of the 'Gala' varieties with a striped defined over colour such as 'Simmons Gala' (U.S. Plant Pat. No. 10,840), 'Burkitt Gala' (U.S. Plant Pat. No. 17,013), 'Baigent' (U.S. Plant Pat. No. 10,016), 'Banning Gala' (U.S. Plant Pat. No. 13,753) and other 'Gala' varieties for the absence of stripes on the dark-purple red over colour (RHS 60A) of 'Gala 2013' fruits.

Asexual reproduction of this new variety by grafting and budding onto rootstock shows that the foregoing and all other characteristics and distinctions remain true to form over successive asexually propagated generations.

BRIEF DESCRIPTION OF THE DRAWINGS

The colours of these illustrations may vary with lighting conditions and, therefore, colour characteristics of this new variety should be determined with reference to the observations described herein, rather than from these illustrations alone.

FIGS. 6 and 7 show fruits on the trees before harvesting, FIG. 8 shows harvested fruits in a box.

DETAILED BOTANICAL DESCRIPTION

The following detailed description of the 'Gala 2013' variety is based on observations made during 2014 growing season in a Griba property 'Gala 2013' planting field in Gazzo Veronese area, in Verona Province (Italy).

Certain characteristics of this variety may change with changing environmental conditions (e.g., light, temperature, moisture), nutrient availability, or other factors. Quantified measurements are expressed as an average of measurements taken from a number of individual plants of the new variety. The measurements of any individual plant, or any group of plants, of the new variety may vary from the stated average. Colour descriptions and other terminology are used in accordance with their ordinary dictionary descriptions, unless the context clearly indicates otherwise. Colour designations are made with reference to The Royal Horticultural Society (R.H.S.) Colour Chart, 5$^{th}$ Edition, 2007.

Figure 1:
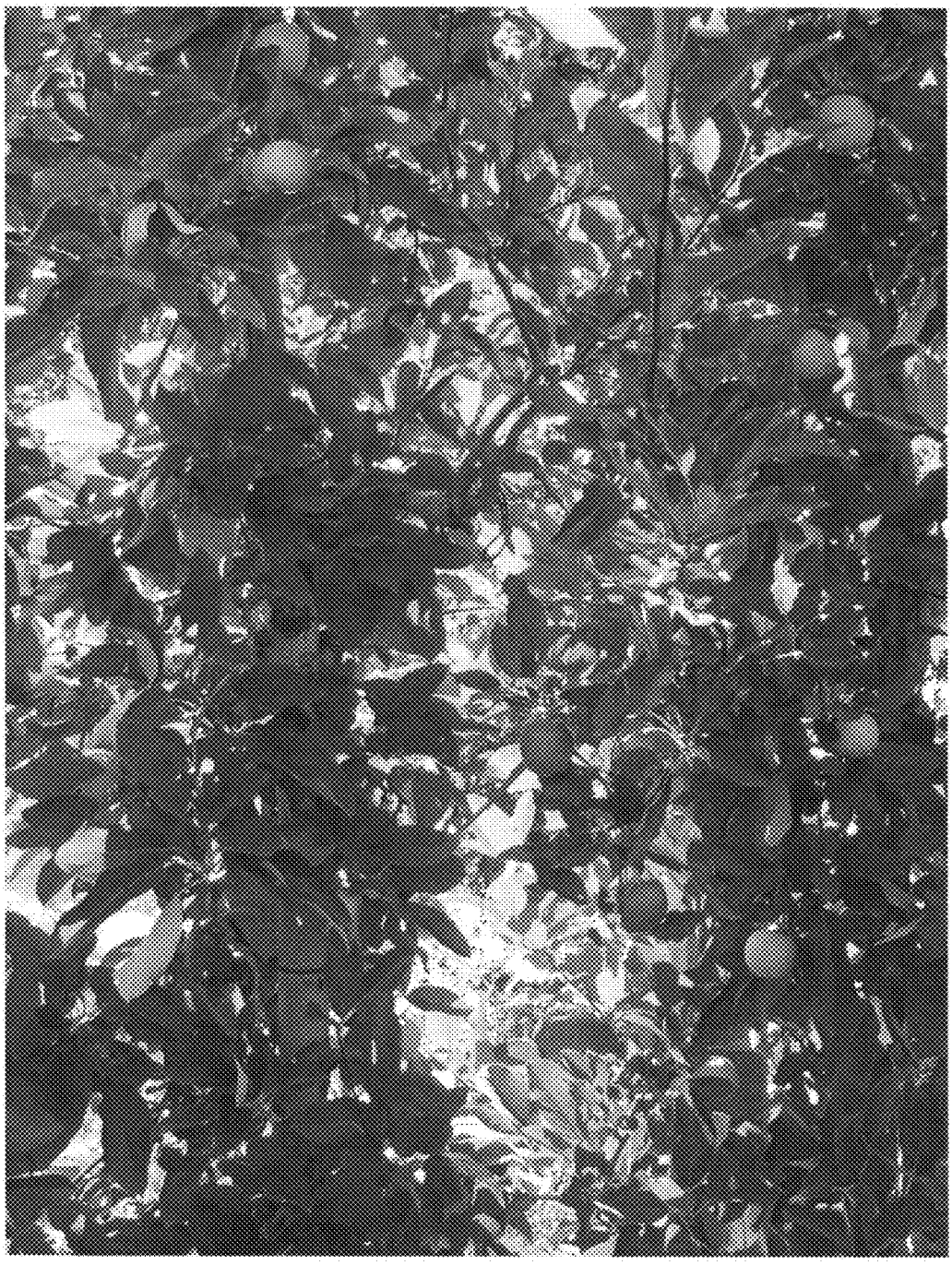
FIG. 1 illustrates the 'Gala Standard' mother tree, 16 years old, with the mutated branch from which 'Gala 2013' has been identified and propagated. At the beginning of July, the apples on the mutated branch are already solid flush red (RHS 5B) compared to the other apples on the tree and the trees around that are still green (RHS 145B).

Parentage: 'Gala 2013' variety originated by a sport limb mutation of a lateral branch of a 'Gala Standard' tree (not patented). The mutation was identified by Mr. Alois Defranceschi in 2009 in his 'Gala' field in Laives area, Bolzano province, Italy. At the beginning of July, 30 days earlier than the picking time, all the apples on the mutated branch appeared solid flush red coloured (RHS 538), while the apples on the rest of the mother tree and the 'Gala Standard' trees around it were still green (RHS 145B) (FIG. 1). At harvesting time the fruits on the mutated branch appeared dark purple red coloured (RHS 60A) on 100% of the surface without stripes, while the other apples on the same tree and the trees around it were 50-70% stripe red coloured (RHS 45A).

Figure 2:
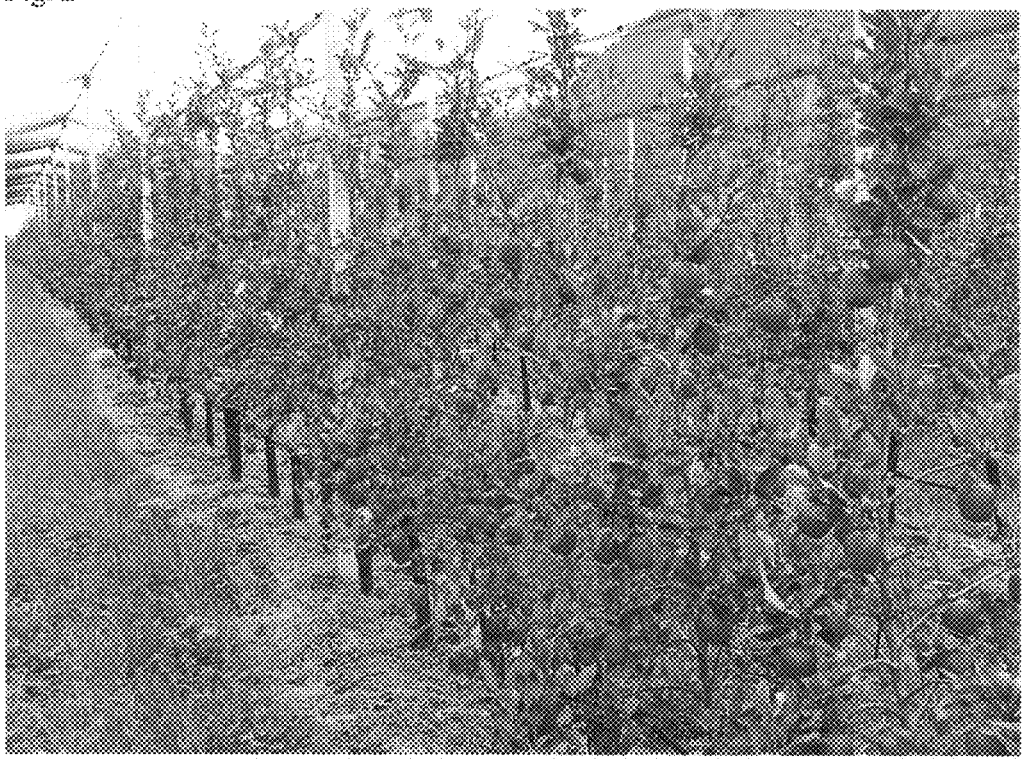
FIG. 2 illustrates 2 year old 'Gala 2013' trees of second generation with fruits at harvesting time.

Tree: the 'Gala 2013' trees here described are two-year old trees grown on M9 rootstock, deriving from the second generation vegetatively propagated 'Gala 2013' mutation; (FIG. 2).

Vigour and overall shape: 'Gala 2013' trees on M9 rootstock show a spreading ramified growth habit with medium vigour, similar to the other 'Gala' clones.

Trunk: Medium stocky; diameter, 28 mm at 200 mm above the graft union; bark texture, smooth; bark colour, grey (RHS 201C).

Primary branches: Basal branches emerge at 400 mm from the grafting point; crotch angle 70° to 90°; bark texture, smooth; bark colour, grey RHS 201C.

Figure 3:
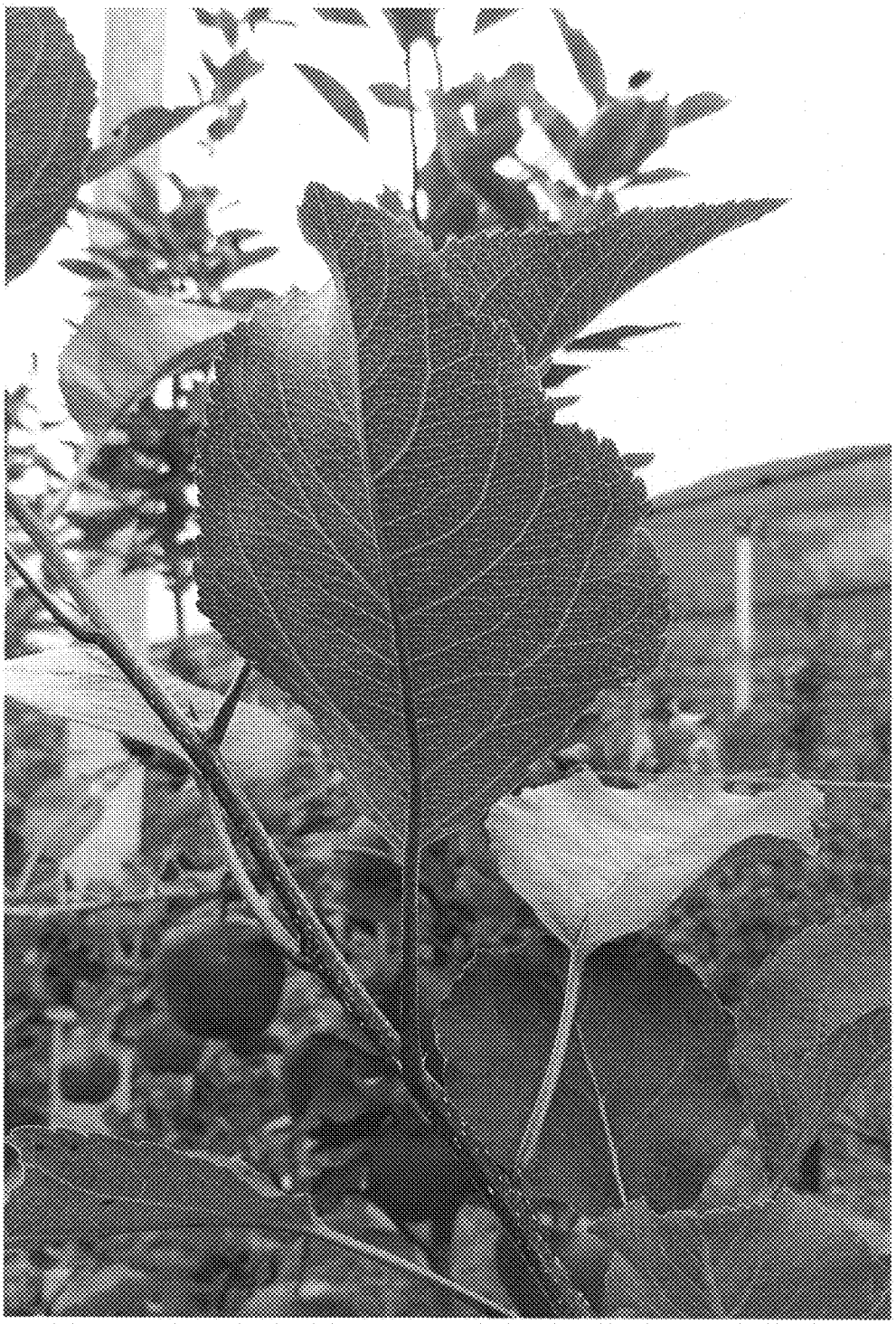
FIG. 3 illustrates a detail of 'Gala 2013' shoot at the end of July and leaves with red petiole and central vein from a 2 year old tree.

One-year old shoot: Length, medium average 260 mm; thickness, 5 mm; internode length, 31 mm; colour at middle of July, greyed-purple RHS N186C; pubescence, absent or very weak; number of lenticels, 6 to 8 per square centimetre; lenticel shape, longitudinal elongated respect to shoot; lenticels colour greyed-white (RHS 156C); (FIG. 3).

Bearing: Annual, abundant, necessity of thinning; flower buds on spurs and shoots; very low or not subjected to alternant bearing.

Hardiness: European hardiness zone 6, comparable to other Gala varieties.

Disease and insect resistance: Susceptibility to classical apple disease comparable to other Gala varieties. No serious pest or disease problems are known to the breeders.

Leaves: Shape, elliptic; length, medium-long 105 mm; width, 58 mm; length/width ratio, 1.8; blade margins, serrate; apex, acute slightly acuminate; colour of upper surface, green (RHS 136A); colour of lower surface, green (RHS 138A); colour of central vein at lower surface, red purple (RHS 61B); pubescence on lower surface, light; pubescence colour, white (RHS N155A); leaf attitude in relation to shoot, outward.

*Petiole*.—Length, medium 34 mm; thickness, medium 2.1 mm; upper surface colour, yellow-green (RHS 148C); lower surface colour, red purple (RHS 61A); petiole pubescence, very weak.

*Stipules*.—Quantity, 2 opposite; shape, thin, little; length 3 mm; colour, yellow-green (RHS 147B) (FIG. 3).

Flowers: Number per cluster, 5 to 6. Unopened flower at balloon stage: length, 12 mm; diameter, 9 mm; shape, round-conical; colour, red-purple (RHS 58B). Open flower: size, medium-small; diameter, 30 mm; pollination requirement, 'Stark Delicious' (not patented), 'Golden Delicious' (not patented), 'Granny Smith' (not patented), 'Braeburn' (not patented), and other varieties flowering at the same period.

Figure 4:
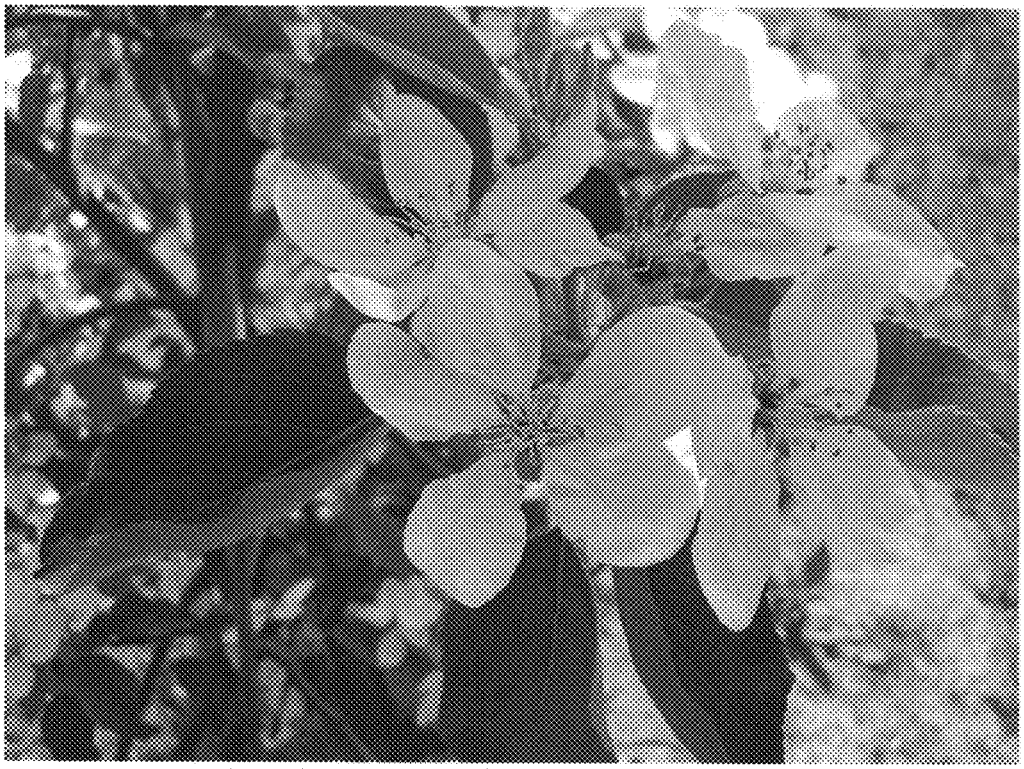
FIG. 4 illustrates the flower of a 2 year old 'Gala 2013' tree at full blooming.

Petals: Number per flower, 5; relative position of petal margins, closed not overlapping; shape, ovoid-elliptic; length, 15 mm; width, 11 mm; apex, rounded; base, conical pointed; margin, smooth; colour of upper surface, white (RHS NN155C) with reddish shades red purple (RHS 64C); colour of lower surface, white (RHS NN155B); (FIG. 4).

Receptacle: Colour at petal abscission, red purple (RHS 60C); (FIG. 4).

Pistil: Size, medium 14 mm long; stigma colour, yellow-green (RHS 145D); styles quantity, 5; style colour, yellow-green (RHS 145C); ovary colour at beginning of flowering, yellow green (RHS 145A); ovary colour at petal abscission, red purple (RHS 61A); (FIG. 4).

Anthers: Quantity 20 to 25 per flower; size, 2.1 mm; presence of pollen; colour of pollen, yellow (RHS 4B).

Pollen: The amount of pollen produced is moderate.

Sepals: Quantity, 5; shape, conical pointed; length, 4 mm; width, 3 mm; colour at beginning of flowering, green (RHS 143A); colour at petal abscission, red (RHS 53A); (FIG. 4).

Pedicel: Length 20 mm; diameter, 1.6 mm; colour, green (RHS 143A).

Bloom season: In 2014 at Gazzo Veronese in Verona Province, Italy, blooming began the 1$^{st}$ of April; full bloom was the 4$^{th}$ of April; finishing on the 8$^{th}$ of April.

Figure 5:
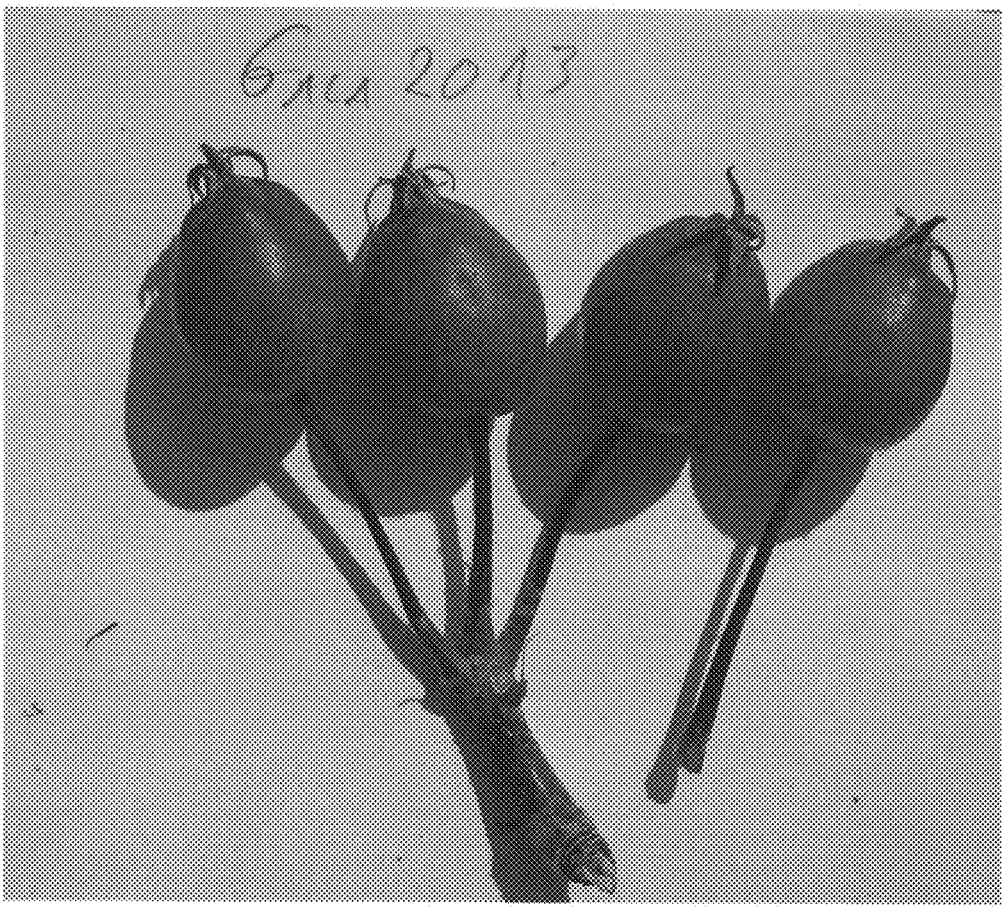
FIG. 5 illustrates the young fruits of a 2 year old 'Gala 2013' tree 40 days after full blooming.

Young fruits (40 days after blooming): Colour, red (RHS 46A); pattern of colour, solid-flush; colour of stalk, greyed-purple (RHS 185A); (FIG. 5).

Fruit: Quantity per cluster, 1 to 3; size, medium; diameter (average of 50 typical fruits), height (average of 50 fruits); 83.6 mm; 76 mm; weight, 196 g; ratio height/width, 1.10; general shape in profile, globose; maximum diameter, in the middle; ribbing, absent; crowning, absent or very week; depth of calyx eye, 5 mm; width of calyx eye, (6 mm); depth of eye basin, medium (8 mm); width of eye basin, medium (27 mm); sepals, closed; length of sepals, medium (4 mm); length of stalk, medium (26 mm); thickness of stalk, 2.3 mm; colour of stalk, greyed-purple (RHS 185A) (FIG. 6); depth of stalk cavity, medium (15 mm); width of stalk cavity, medium (31 mm); ground color: red (RHS53A); small presence of russet around the stalk cavity, limited to the deepest part of the cavity.

Fruit skin at harvest: Sense to the touch, smooth, slightly waxy; bloom, absent or very weak; greasiness, absent or very weak; thickness, thin; russet around stalk cavity, present weak; russet around the calyx eye, absent or very weak; number of checks per square cm, 6 to 7; shape of cheeks, round-irregular; size of cheeks, around 0.5 mm; colour of cheeks, white (RHS NN155D); russet around cheeks, very limited.

Figure 6:
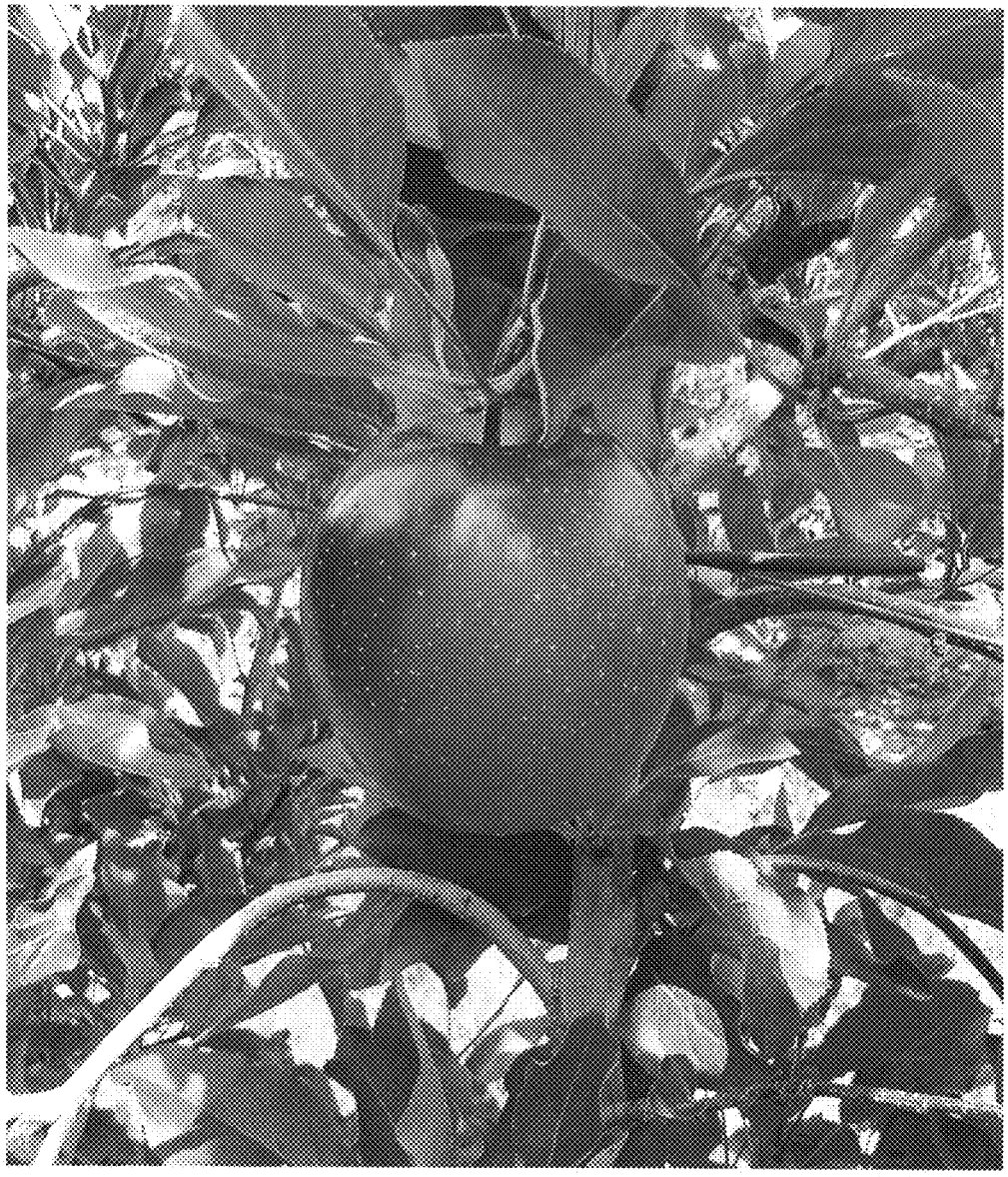
FIGS. 6, 7 and 8 illustrate 'Gala 2013' fruits from 2 year old trees at harvesting time.
Figure 7:
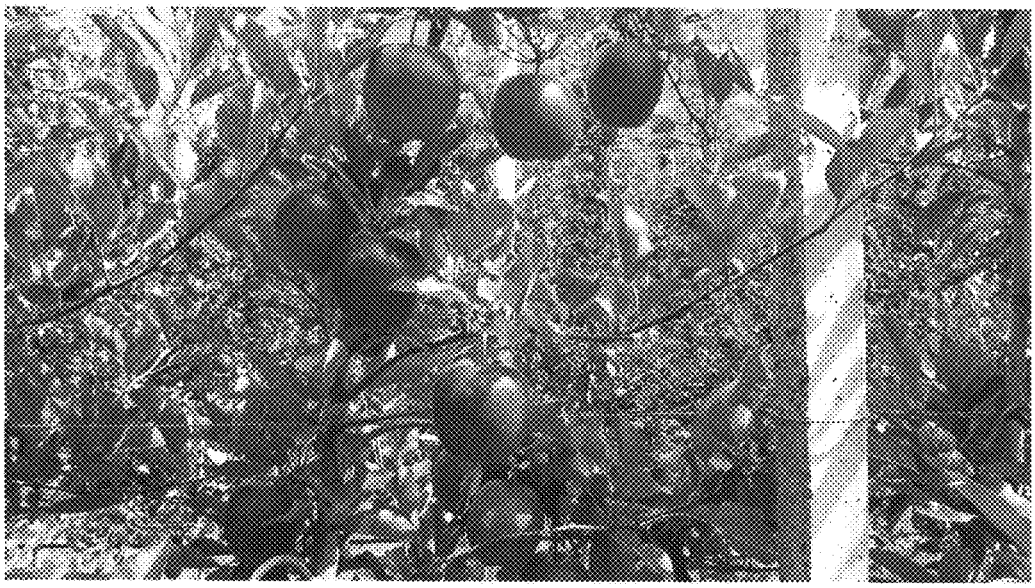
Figure 8:
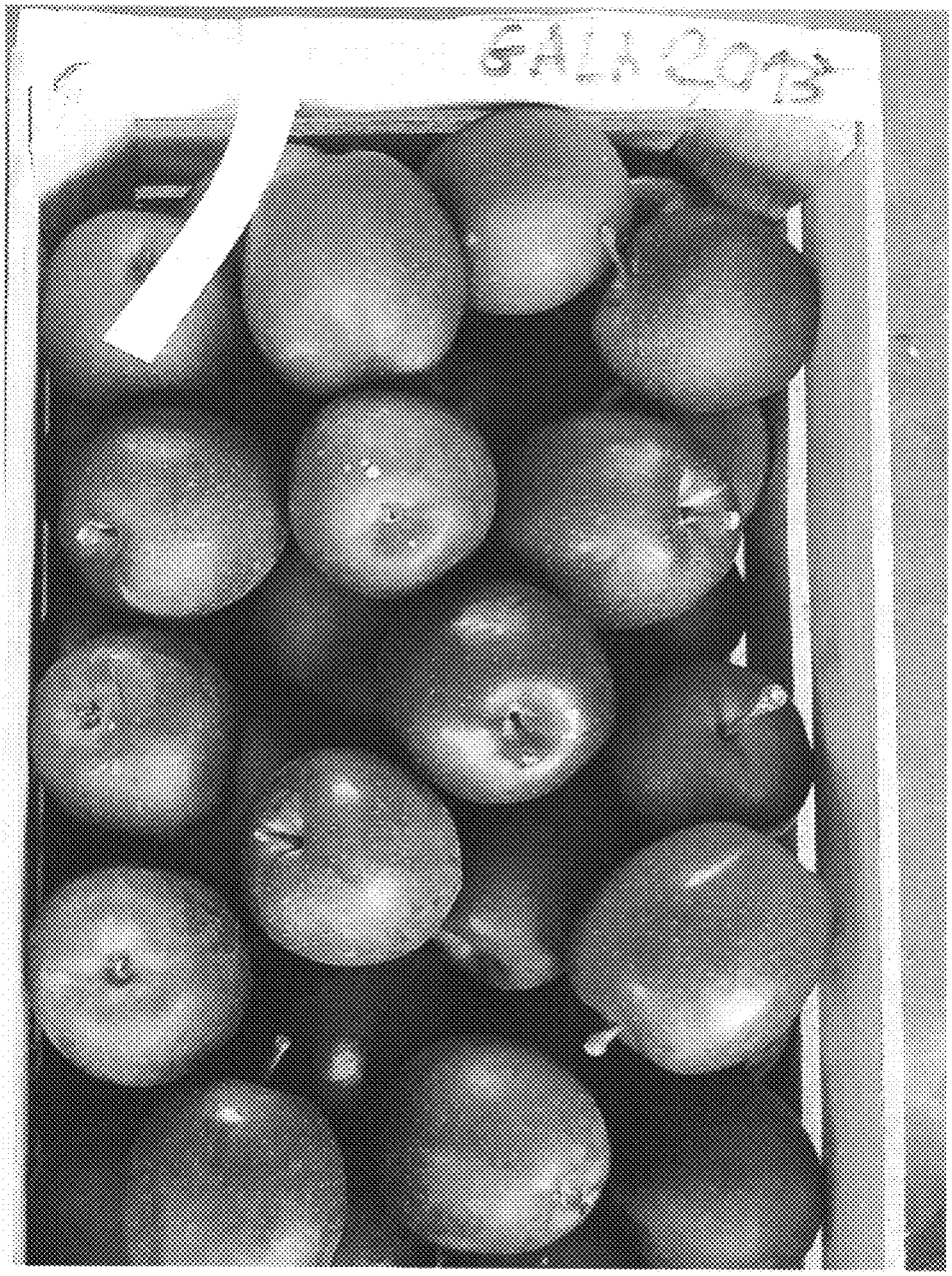

Fruit skin colour at harvest: Background colour, red (RHS 53A); pattern of over-colour, solid flush; over colour of skin, red purple (RHS 60A); amount of over colour, 95 to 100% fruit coverage; intensity of over-colour, dark; (FIGS. 6, 7, and 8).

Figure 10:
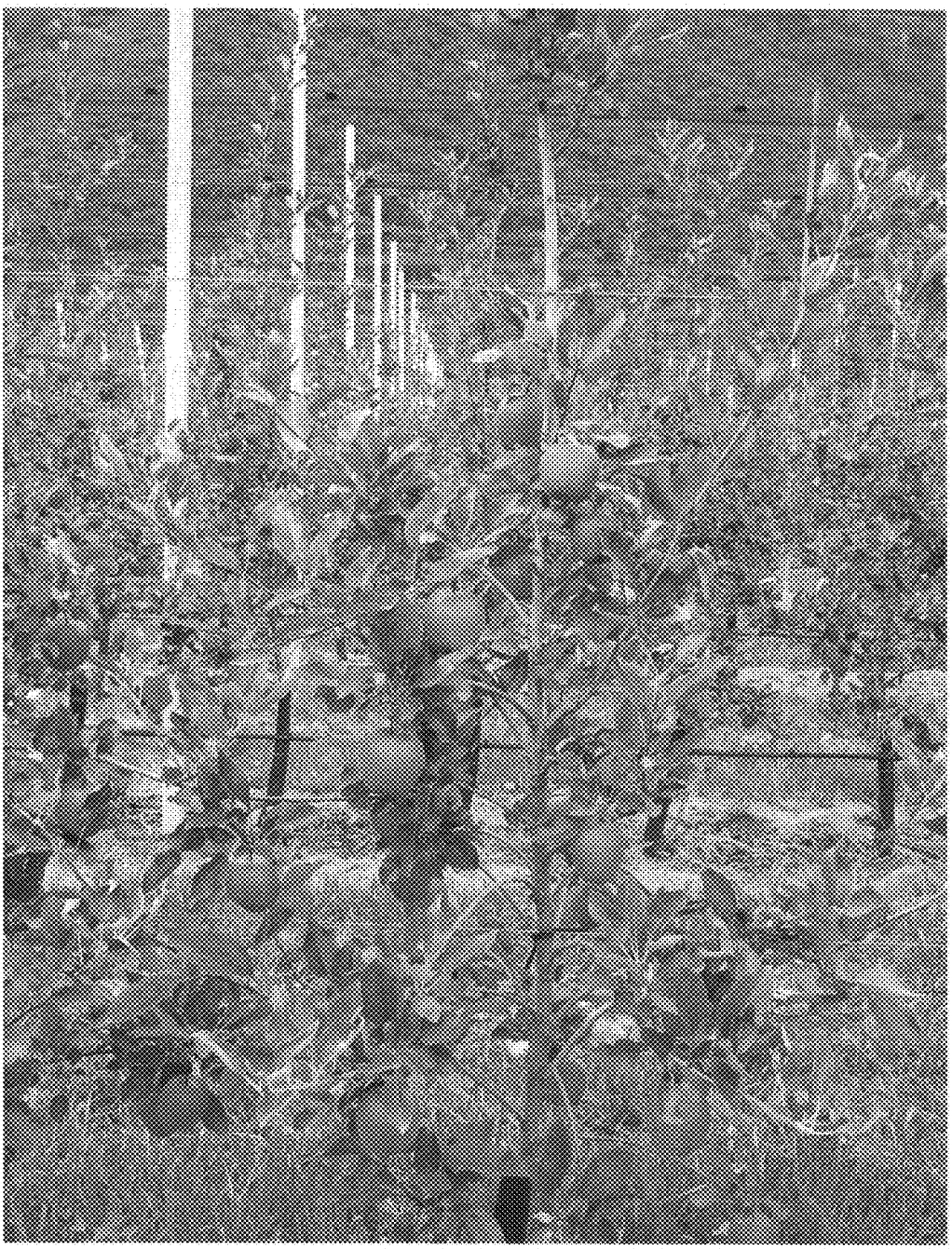
FIG. 10 illustrates a two-year old 'Gala 2013' tree with the red coloured (RHS 53B) fruits 30 days before harvesting.

Fruit appearance 30 days before harvest: Colour, red (RHS 53B); pattern of colour, solid flush; amount of colour, 90% fruit coverage; (FIG. 10).

Fruit flesh: Firmness, medium to firm; texture, fine; colour, light yellow (RHS 11D); flesh colour 1 mm under the skin, pale red (RHS 53C), (FIG. 9); flavour, sweet; at harvest time 11-11.5 Brix and 4.7-5.2 g/l acidity; aroma, good and intense aroma classical of the original 'Gala'; juiciness, moderately-juicy.

Figure 9:
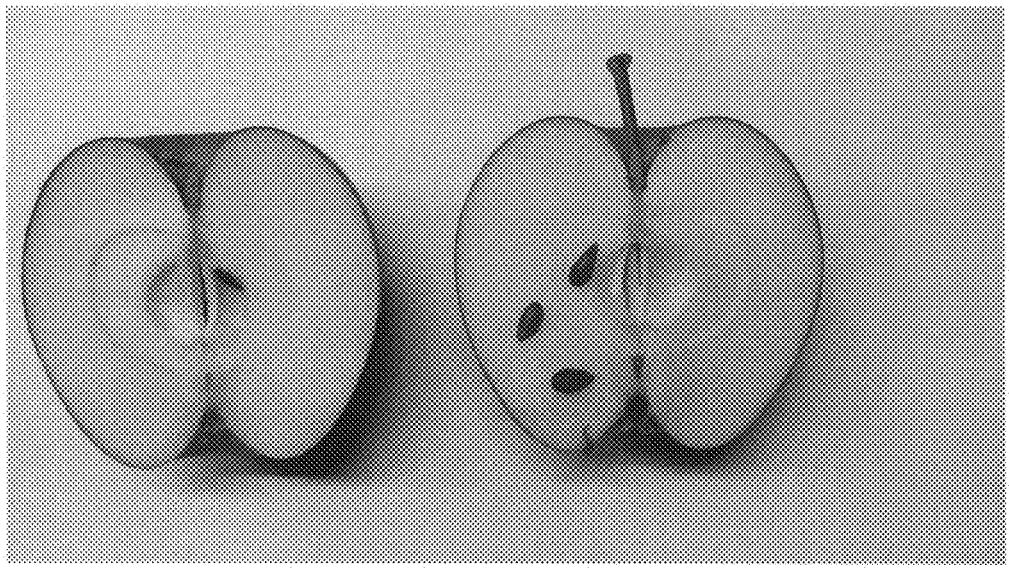
FIG. 9 illustrates the flesh of a fruit from a 2 year old 'Gala 2013' tree' on the longitudinal section and the seeds.

Fruit core: Locules, five to six moderately open; seeds, 1 to 2 per locule, shape of seed, oval elongated; colour of seeds, brown greyed-orange (RHS 166A); (FIG. 9).

Fruit picking time: In 2014 at Gazzo Veronese in Verona Province, Italy, the first picking of 'Gala 2013' began the 5$^{th}$ of August (30 days earlier than 'Golden Delicious') where the complete dark purple-red coloration of the apple permitted the harvesting of all the fruits in one picking.

Eating maturity: The time of eating maturity begis with the picking time, about the 5th of August; the variety can be stored in cold storage till January. The market use of the fruit of 'Gala 2013' is in the fresh market.

What is claimed is:

1. A new and distinct tree of *Malus domestica* Borkh named 'Gala 2013', substantially as illustrated and described herein.

* * * * *